United States Patent
Imagawa et al.

(10) Patent No.: US 9,888,898 B2
(45) Date of Patent: Feb. 13, 2018

(54) X-RAY DIAGNOSTIC APPARATUS

(71) Applicant: Toshiba Medical Systems Corporation, Otawara-shi (JP)

(72) Inventors: Kazuo Imagawa, Nasushiobara (JP); Takuya Sakaguchi, Utsunomiya (JP); Ryuji Zaiki, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 398 days.

(21) Appl. No.: 14/659,864

(22) Filed: Mar. 17, 2015

(65) Prior Publication Data
US 2015/0272529 A1 Oct. 1, 2015

(30) Foreign Application Priority Data

Mar. 27, 2014 (JP) .................... 2014-066768

(51) Int. Cl.
*A61B 6/00* (2006.01)
*A61B 6/03* (2006.01)
(Continued)

(52) U.S. Cl.
CPC .......... *A61B 6/5247* (2013.01); *A61B 5/0035* (2013.01); *A61B 5/02007* (2013.01);
(Continued)

(58) Field of Classification Search
CPC ......... A61B 6/032; A61B 6/469; A61B 6/504; A61B 6/5205; A61B 6/5247; A61B 6/547;
(Continued)

(56) References Cited

U.S. PATENT DOCUMENTS 5,293,574 A * 3/1994 Roehm ............... A61B 6/504
378/98.2
8,625,865 B2 1/2014 Zarkh et al.
(Continued)

FOREIGN PATENT DOCUMENTS

JP 2008-514265 5/2008
JP 2008-516722 5/2008
(Continued)

OTHER PUBLICATIONS

Japanese Office Action dated Nov. 14, 2017 in Japanese Application No. 2014-066768 (4 pages).

*Primary Examiner* — Glen Kao
(74) *Attorney, Agent, or Firm* — Oblon, McClelland, Maier & Neustadt, L.L.P.

(57) ABSTRACT

The X-ray diagnostic apparatus includes an X-ray emitting device, an X-ray detection device, a fluoroscopic image generating unit, a calcified region detection unit and a display control unit. The fluoroscopic image generating unit generates a plurality of frames of fluoroscopic images of an object on a basis of detected X-rays in sequence. The calcified region detection unit detects a calcified region on each of the fluoroscopic images in sequence. The display control unit superimposes a calcified region image on a position of the calcified region on each of the fluoroscopic images in sequence, the calcified region image including a calcified region on a pre-acquired CT image or MR image of the object, and displays resulting images on a display device in sequence.

19 Claims, 16 Drawing Sheets

(51) Int. Cl.
 *A61B 5/02* (2006.01)
 *A61B 5/00* (2006.01)
(52) U.S. Cl.
 CPC ............ *A61B 5/4887* (2013.01); *A61B 6/032* (2013.01); *A61B 6/4441* (2013.01); *A61B 6/469* (2013.01); *A61B 6/504* (2013.01); *A61B 6/5205* (2013.01); *A61B 6/547* (2013.01); *A61B 6/4283* (2013.01)
(58) Field of Classification Search
 CPC . A61B 5/0035; A61B 5/0037; A61B 5/02007; A61B 5/055; A61B 5/4887; A61B 6/4441
 See application file for complete search history.

(56) References Cited

U.S. PATENT DOCUMENTS

| | | | | |
|---|---|---|---|---|
| 2011/0075900 | A1* | 3/2011 | Masumoto | G06F 19/321 382/128 |
| 2012/0148135 | A1* | 6/2012 | Van Rens | G06T 7/194 382/131 |
| 2012/0177277 | A1* | 7/2012 | Florent | A61B 5/02007 382/132 |

FOREIGN PATENT DOCUMENTS

| | | |
|---|---|---|
| JP | 2013-505786 | 2/2013 |
| JP | 2013-158372 | 8/2013 |

\* cited by examiner

X-RAY DIAGNOSTIC APPARATUS

CROSS-REFERENCE TO RELATED APPLICATION

This application is based upon and claims the benefit of priority from Japanese Patent Application No. 2014-66768, filed on Mar. 27, 2014, the entire contents of which are incorporated herein by reference.

FIELD

An embodiment as one aspect of the present invention relates to an X-ray diagnostic apparatus.

BACKGROUND

Recently, aortic valve replacement procedures using a catheter (TAVI (trans-catheter aortic valve implantation) or TAVR (trans-catheter aortic valve replacement)) have been attracting attention. The aortic valve replacement procedure is carried out, for example, in a procedure room equipped with an X-ray diagnostic apparatus. That is, the aortic valve replacement procedure is a technique for placing an artificial valve in a heart of an object while observing fluoroscopic images collected by the X-ray diagnostic apparatus in real time.

With the aortic valve replacement procedure, it is important to place the artificial valve at a precise location by referring to fluoroscopic images. Specifically, an aim is to place the artificial valve such that a lower end of the artificial valve will be below a bottom of a natural valve and that an upper end of the artificial valve will be above a tip of the natural valve leaflet and below a coronary arteries.

A technique has been disclosed which displays a fused image based on an angiographic image and fluoroscopic image of the object.

In the aortic valve replacement procedure, if there is a calcified area on a coronary artery wall, when the catheter is advanced, a tip of the catheter may sometimes come into contact with the calcified area. When placed in contact with a distal end of the catheter, the calcified area can separate from the coronary artery wall and flow through the coronary arteries, causing cerebral infarction as a complication.

To prevent the distal end of the catheter from coming into contact with calcified areas, it is necessary to present appropriate real-time images to a surgeon, and a conventional technique displays images obtained by fusing an entire angiographic image with real-time fluoroscopic images using a bone or the like as a landmark. With such a conventional fused image since there is a deviation between the fluoroscopic image and angiographic image in coronary artery location which moves along with heartbeats, it is very difficult to prevent the distal end of the catheter from coming into contact with calcified areas by watching the fused image.

BRIEF DESCRIPTION OF THE DRAWINGS

In accompanying drawings.

DETAILED DESCRIPTION

An X-ray diagnostic apparatus according to an embodiment of the present invention will be described with reference to the accompanying drawings.

To solve the above-described problems, the present embodiment provides the X-ray diagnostic apparatus, including: an X-ray emitting device configured to generate X-rays; an X-ray detection device placed facing the X-ray emitting device and configured to detect the X-rays; a fluoroscopic image generating unit configured to generate a plurality of frames of fluoroscopic images of an object on a basis of the detected X-rays in sequence; a calcified region detection unit configured to detect a calcified region on each of the fluoroscopic images in sequence; and a display control unit configured to superimpose a calcified region image on a position of the calcified region on each of the fluoroscopic images in sequence, the calcified region image including a calcified region on a pre-acquired CT image or MR image of the object, and to display resulting images on a display device in sequence.

Figure 1:
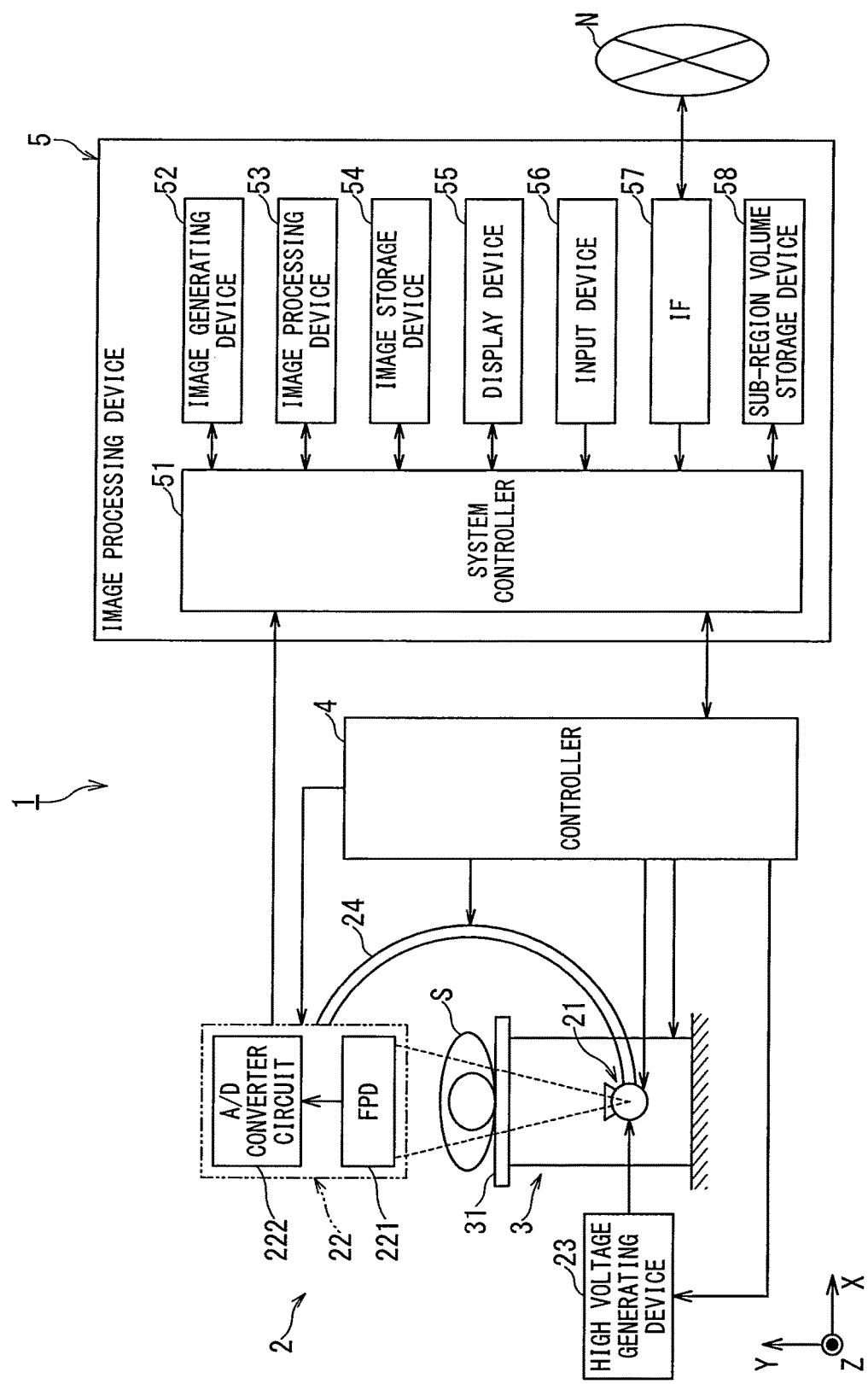
FIG. 1 is a schematic diagram illustrating a configuration of an X-ray diagnostic apparatus according to a present embodiment.
Figure 2:
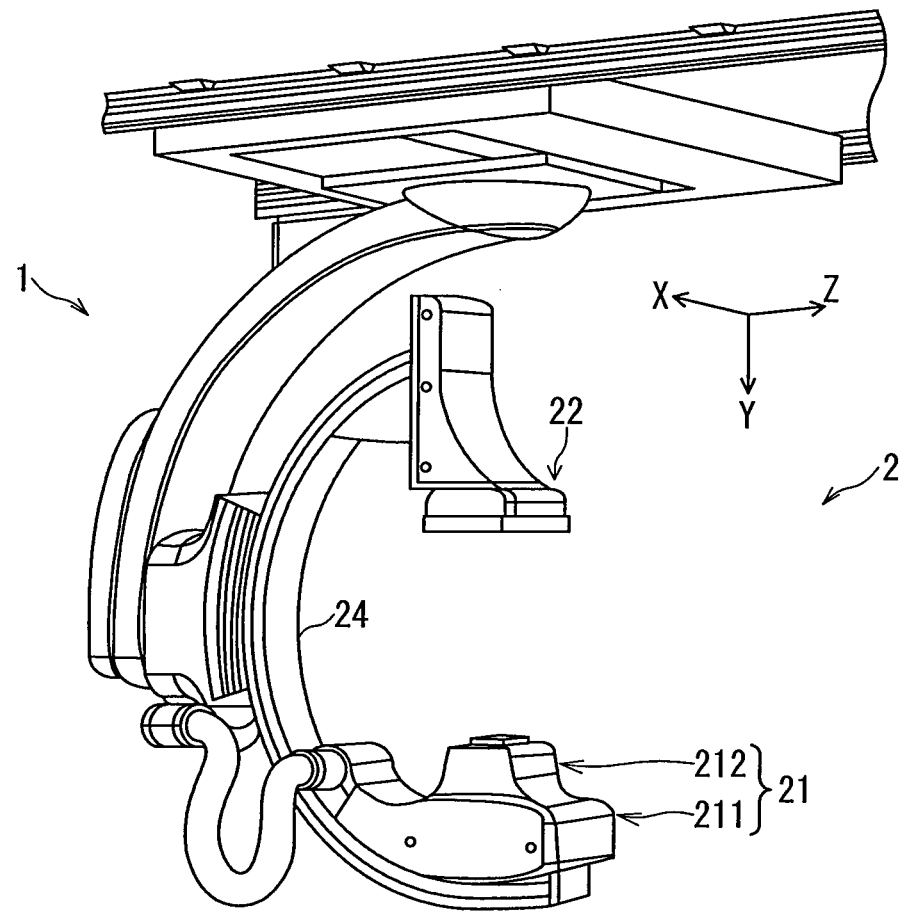
FIG. 2 is a perspective view illustrating an external configuration of the X-ray diagnostic apparatus according to the present embodiment when the X-ray diagnostic apparatus is equipped with an overhead travelling C-arm.

FIG. 1 is a schematic diagram illustrating a configuration of the X-ray diagnostic apparatus according to the present embodiment. FIG. 2 is a perspective view illustrating an external configuration of the X-ray diagnostic apparatus according to the present embodiment when the X-ray diagnostic apparatus is equipped with an overhead travelling C-arm.

FIGS. 1 and 2 show an X-ray diagnostic apparatus 1 used for trans-catheter procedures such as an aortic valve replacement (TAVI or TAVR) procedure in the present embodiment. The X-ray diagnostic apparatus 1 is applicable not only to aortic valve replacement procedures, but also to procedures, such as stenting, which need to avoid contact between a distal end of the catheter and calcified areas.

The X-ray diagnostic apparatus 1 largely includes an imaging device 2, a bed system 3, a controller 4, and an image processing device (digital fluorography (DF) apparatus) 5. The imaging device 2, bed system 3, and controller 4 are generally installed in a surgical operating room (examination/treatment room) while the image processing device 5 is installed in a control room located next to the surgical operating room.

The imaging device 2 includes an X-ray emitting device 21, an X-ray detection device 22, a high voltage generating device 23, and a C-arm 24.

The X-ray emitting device 21 is installed at one end of the C-arm 24. The X-ray emitting device 21 is configured to be able to move forward and backward under control of the controller 4. The X-ray emitting device 21 includes an X-ray tube (an X-ray source) 211 and a movable beam limiting device 212 as illustrated in FIG. 2.

The X-ray tube 211 is supplied with high voltage power from the high voltage generating device 23 and generates X-rays according to conditions of the high voltage power.

The movable beam limiting device 212 movably supports aperture blades made of a material which blocks X-rays at an X-ray emission aperture of the X-ray tube 211. Note that a radiation quality adjustment filter (not illustrated) configured to adjust radiation quality of the X-rays generated by the X-ray tube 211 may be provided on a front of the X-ray tube 211.

The X-ray detection device 22 is installed at another end of the C-arm 24, facing the X-ray emitting device 21. The X-ray detection device 22 is configured to be able to move forward and backward under the control of the controller 4. The X-ray detection device 22 includes an FPD (flat panel detector) 221 and an A/D (analog to digital) converter circuit 222.

The FPD 221 includes a plurality of detecting elements arranged two-dimensionally. A signal line and scanning line are disposed at right angles to each other between each pair of the detecting elements of the FPD 221. Note that a grid (not illustrated) may be provided on a front of the FPD 221. To absorb scattered radiation incident on the FPD 221 and improve contrast of X-ray images, the grid includes grid plates made of lead or the like with high X-ray absorption and aluminum, wood, or the like transparent to X-rays, with the grid plates and aluminum or wood being arranged alternately.

The A/D converter circuit 222 converts projection data of a time-series analog signal (video signal) outputted from the FPD 221 into digital signal, and outputs the digital signal to the image processing device 5.

Note that the X-ray detection device 22 may be an I.I. (image intensifier)-TV system. The I.I.-TV system converts X-rays transmitted through the object S and directly entering X-rays into visible light and doubles luminance in the process of light-electron-light conversion, thereby forming projection data of high sensitivity. Then, the I.I.-TV system converts the optical projection data into an electrical signal using a CCD (charge coupled device) image element.

The high voltage generating device 23 is capable of supplying high voltage power to the X-ray tube 211 of the X-ray emitting device 21 under the control of the controller 4.

The C-arm 24 places the X-ray emitting device 21 and X-ray detection device 22 on opposite sides of the object S, facing each other. Under the control of the controller 4, the C-arm 24 causes the X-ray emitting device 21 and X-ray detection device 22 to make arcing motions as an integral unit along an arc direction of the C-arm 24. Note that although description is given here of an example in which the X-ray diagnostic apparatus 1 is equipped with the C-arm 24, which is configured to cause the X-ray emitting device 21 and X-ray detection device 22 to operate as an integral unit, this is not restrictive. For example, without being equipped with the C-arm 24, the X-ray diagnostic apparatus 1 may be configured to cause the X-ray emitting device 21 and X-ray detection device 22 to operate independently of each other.

The bed system 3 is supported on a floor surface, and supports a table (catheter table) 31. Under the control of the controller 4, the bed system 3 causes the table 31 to make sliding motions (in X- and Z-axis directions), up-and-down motions (in a Y-axis direction), and rolling motions. The table 31 allows the object S to be placed thereon. Note that although the imaging device 2 is described by assuming that the X-ray emitting device 21 is an under-tube type located below the table 31, the imaging device 2 is also applicable when the X-ray emitting device 21 is an over-tube type located above the table 31.

The controller 4 includes a processing circuit (CPU: central processing unit) and a memory (neither is illustrated). Under control of the image processing device 5, the controller 4 controls driving of the X-ray emitting device 21, X-ray detection device 22, and C-arm 24 on the imaging device 2 as well as driving of the bed system 3, for the purpose of alignment. Under the control of the image processing device 5, the controller 4 controls operation of the X-ray emitting device 21, X-ray detection device 22, and high voltage generating device 23, for surgery-related X-ray radiography (fluorography).

The image processing device 5 is constructed based on a computer and is configured to perform operation control of the entire X-ray diagnostic apparatus 1 as well as to perform image processing of plural X-ray images (X-ray image data) acquired by the imaging device 2, etc. The image processing device 5 includes a system controller 51, an X-ray image generating device 52, an X-ray image processing device 53, an X-ray image storage device 54, a display device 55, an input device 56, an IF (interface) 57, and a sub-region volume storage device 58.

The system controller 51 includes a CPU and memory (neither is illustrated). The system controller 51 controls the controller 4 as well as the components 52 to 58.

Under control of the system controller 51, the X-ray image generating device 52 applies a logarithmic transformation process (LOG process) to the projection data outputted from the A/D converter circuit 222 on the imaging device 2, performs an addition process as required, and thereby generates X-ray images.

Under the control of the system controller 51, the X-ray image processing device 53 applies image processing to the X-ray images generated by the X-ray image generating device 52. Examples of image processing include expansion, gradation processing, and spatial filtering of data; minimum value and maximum value tracing of data accumulated in time sequence; and addition intended to remove noise. Note that the data subjected to image processing by the X-ray image processing device 53 is stored in the X-ray image storage device 54.

The display device 55 is made up of a liquid crystal display or CRT (cathode ray tube), etc. Under the control of the system controller 51, the display device 55 displays after-mentioned various image data together with text information and scales of various parameters based on a video signal.

The input device 56 includes a keyboard and mouse which can be manipulated by an operator such as a surgeon, and an input signal corresponding to a manipulation is sent to the system controller 51.

The IF 57 is made up of connectors compliant with parallel connection specifications and serial connection specifications. The IF 57 has a function to connect to a network N via a telephone line through communications control in accordance with appropriate standard and thereby allows the image processing device 5 to be connected to the network N.

The sub-region volume storage device 58 stores calcified regions (described later) generated by MR angiography (MRA) or CT angiography (CTA).

Figure 3:
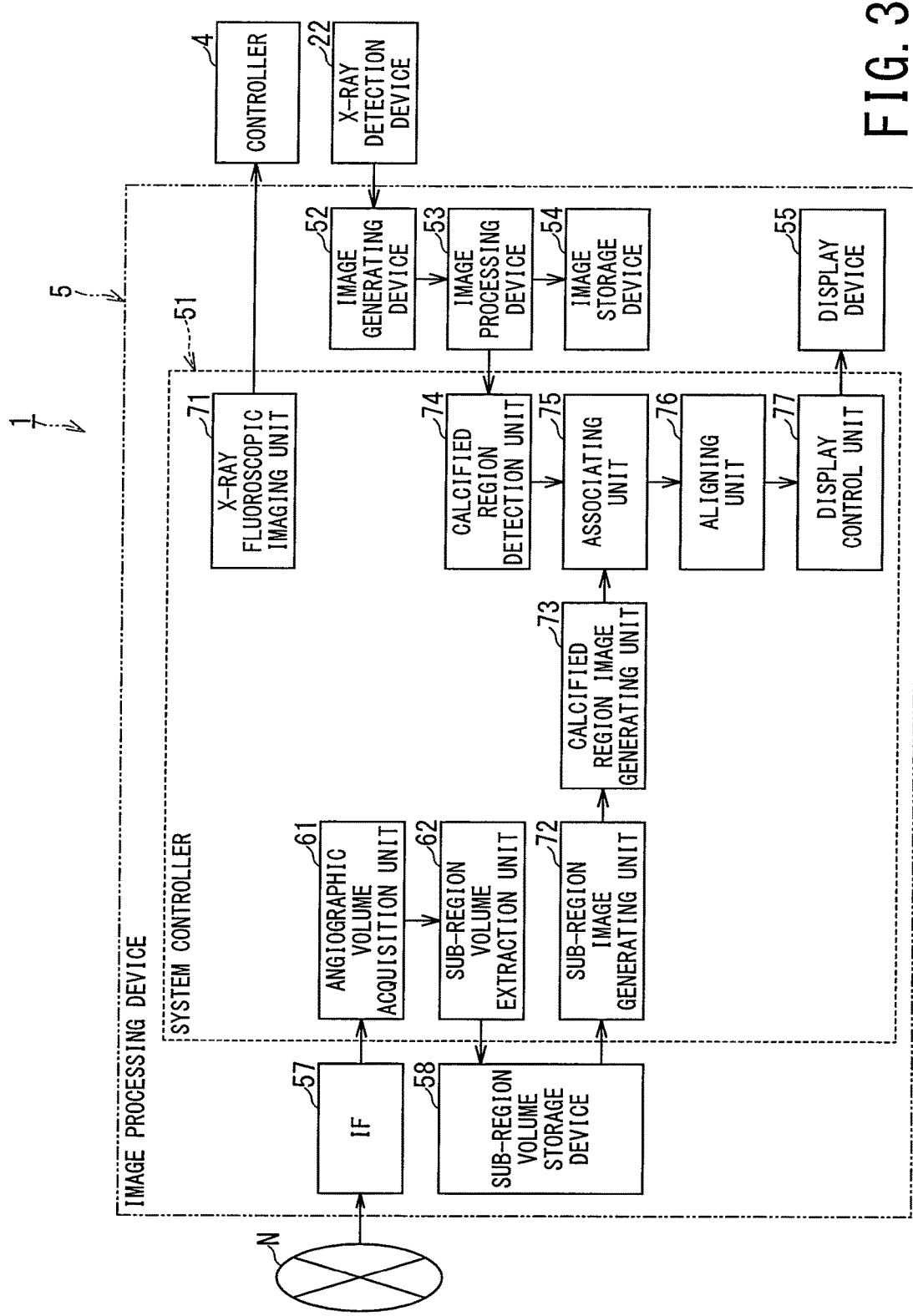
FIG. 3 is a block diagram illustrating functions of the X-ray diagnostic apparatus according to the present embodiment.

FIG. 3 is a block diagram illustrating functions of the X-ray diagnostic apparatus 1 according to the present embodiment.

As the system controller 51 illustrated in FIG. 1 executes a program, the X-ray diagnostic apparatus 1 functions as an angiographic volume acquisition unit 61, a sub-region volume extraction unit 62, an X-ray fluoroscopic imaging unit 71, a sub-region image generating unit 72, a calcified region image generating unit 73, a calcified region detection unit 74, an associating unit 75, an aligning unit 76 and a display control unit 77, as illustrated in FIG. 3. Note that although it has been stated that the units 61, 62, and 71 to 77 making up the X-ray diagnostic apparatus 1 function when a program is executed, this is not restrictive. All or part of the units 61, 62, and 71 to 77 making up the X-ray diagnostic apparatus 1 may be provided as hardware such as a circuit on the X-ray diagnostic apparatus 1.

Note that whereas the units 61 and 62 making up the X-ray diagnostic apparatus 1 function in advance before surgery-related X-ray fluoroscopy, the units 71 to 77 making up the X-ray diagnostic apparatus 1 function during the surgery-related X-ray fluoroscopy.

The angiographic volume acquisition unit 61 has a function to acquire an angiographic volume (angiographic volume data) of a chest including the aorta (including the descending aorta, aortic arch, and ascending aorta) of the object S (illustrated in FIG. 1) from the network N via the IF 57. For example, the angiographic volume acquisition unit 61 acquires the angiographic volume generated by MR angiography (MRA) or CT angiography (CTA).

Figure 4:
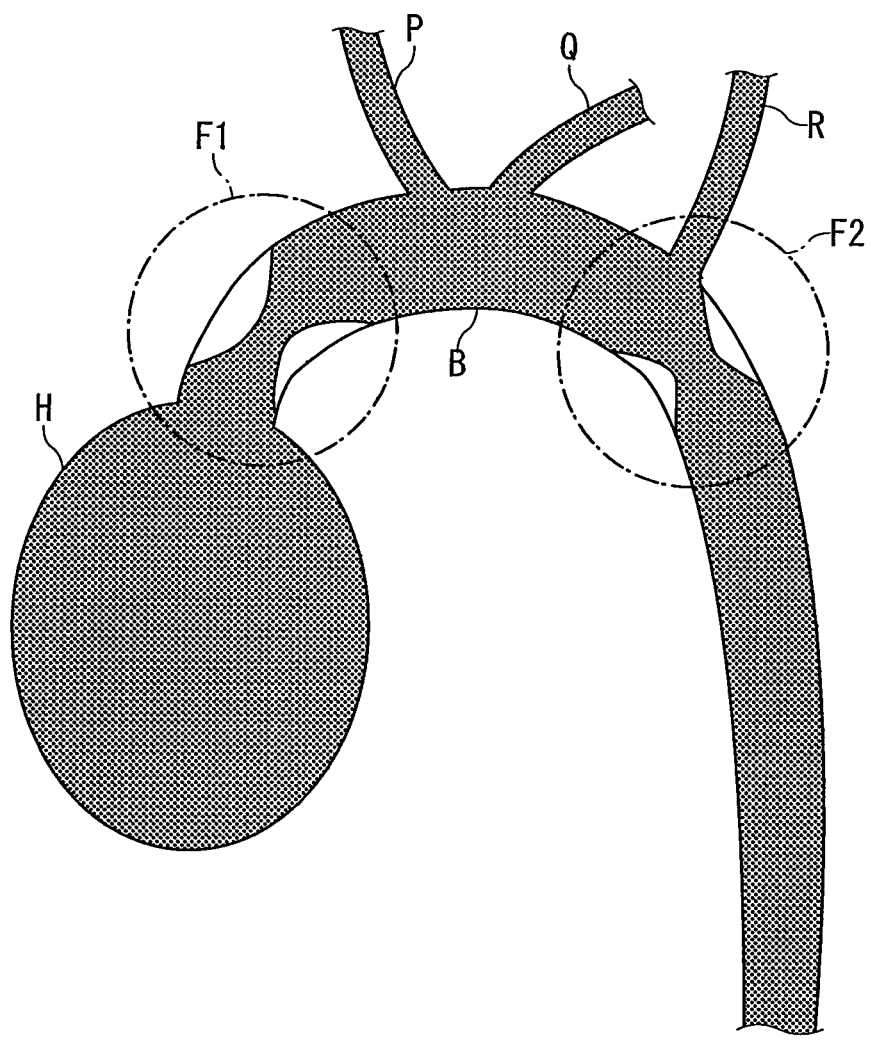
FIG. 4 is a diagram illustrating an example of an angiographic volume.

FIG. 4 is a diagram illustrating an example of the angiographic volume.

FIG. 4 shows the angiographic volume two-dimensionally. As illustrated in FIG. 4, the angiographic volume includes a heart region H, an aortic arch region B of the aorta above the heart region H, as well as a BCA region P, an LCA region Q, and an LSCA region R, which are branch arteries branching off from the aortic arch region B.

Returning to the description of FIG. 3, the sub-region volume extraction unit 62 has a function to extract a sub-region volume (sub-region volume data) related to sub-regions, based on the angiographic volume acquired by the angiographic volume acquisition unit 61. The sub-region volume extraction unit 62 has a function to register a sub-region volume (sub-region volume data) in the sub-region volume storage device 58.

The sub-region volume extraction unit 62 extracts the sub-region volume either based on a well-known technique or based on a region entered via the input device 56 (illustrated in FIG. 1) on an image which is based on the angiographic volume and displayed on the display device 55. Alternatively, the sub-region volume extraction unit 62 extracts high-curvature regions (sub-regions F1 and F2 (illustrated in FIG. 4)) as sub-region volumes from the aortic arch region B (illustrated in FIG. 4) based on the angiographic volume, where the high-curvature regions have a curvature factor of the aortic arch region higher than a threshold and are prone to get calcified.

The X-ray fluoroscopic imaging unit 71 has a function to perform alignment by driving the imaging device 2 and bed system 3 (both illustrated in FIG. 1) via the controller 4 in response to a command entered via the input device 56 (illustrated in FIG. 1) after the object S (both illustrated in FIG. 1) is put on the table 31 of the imaging device 2. The X-ray fluoroscopic imaging unit 71 has a function to collect a plurality of frames (1st, 2nd, . . . , T-th) of fluoroscopic images in sequence via the X-ray image processing device 53 by performing surgery-related X-ray fluoroscopy with respect to the chest of the object S including the aorta by operating the X-ray emitting device 21, X-ray detection device 22, and high voltage generating device 23 (all illustrated in FIG. 1). The plural frames of fluoroscopic images generated by the X-ray image processing device 53 are stored in the X-ray image storage device 54.

Figure 5:
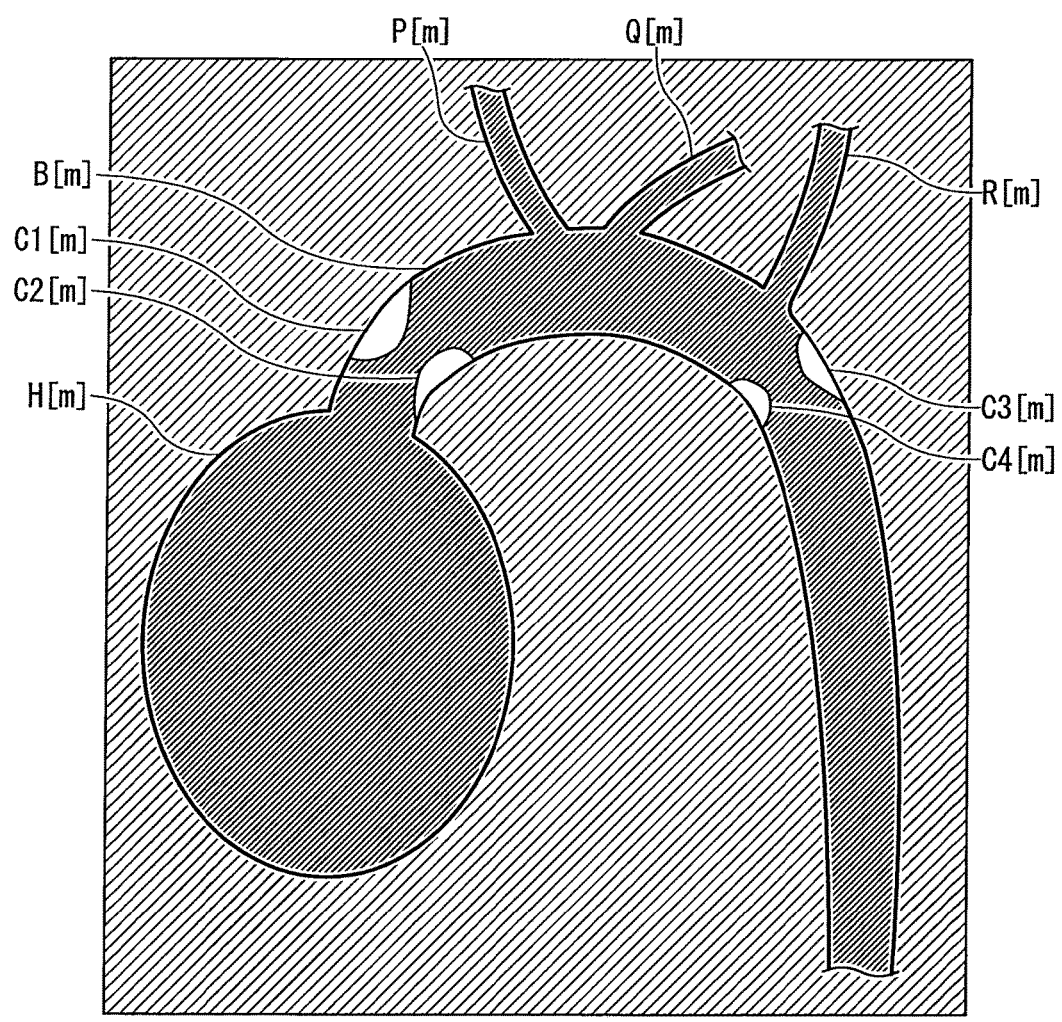
FIG. 5 is a diagram illustrating an example of a fluoroscopic image of an end-diastolic heart.
Figure 6:
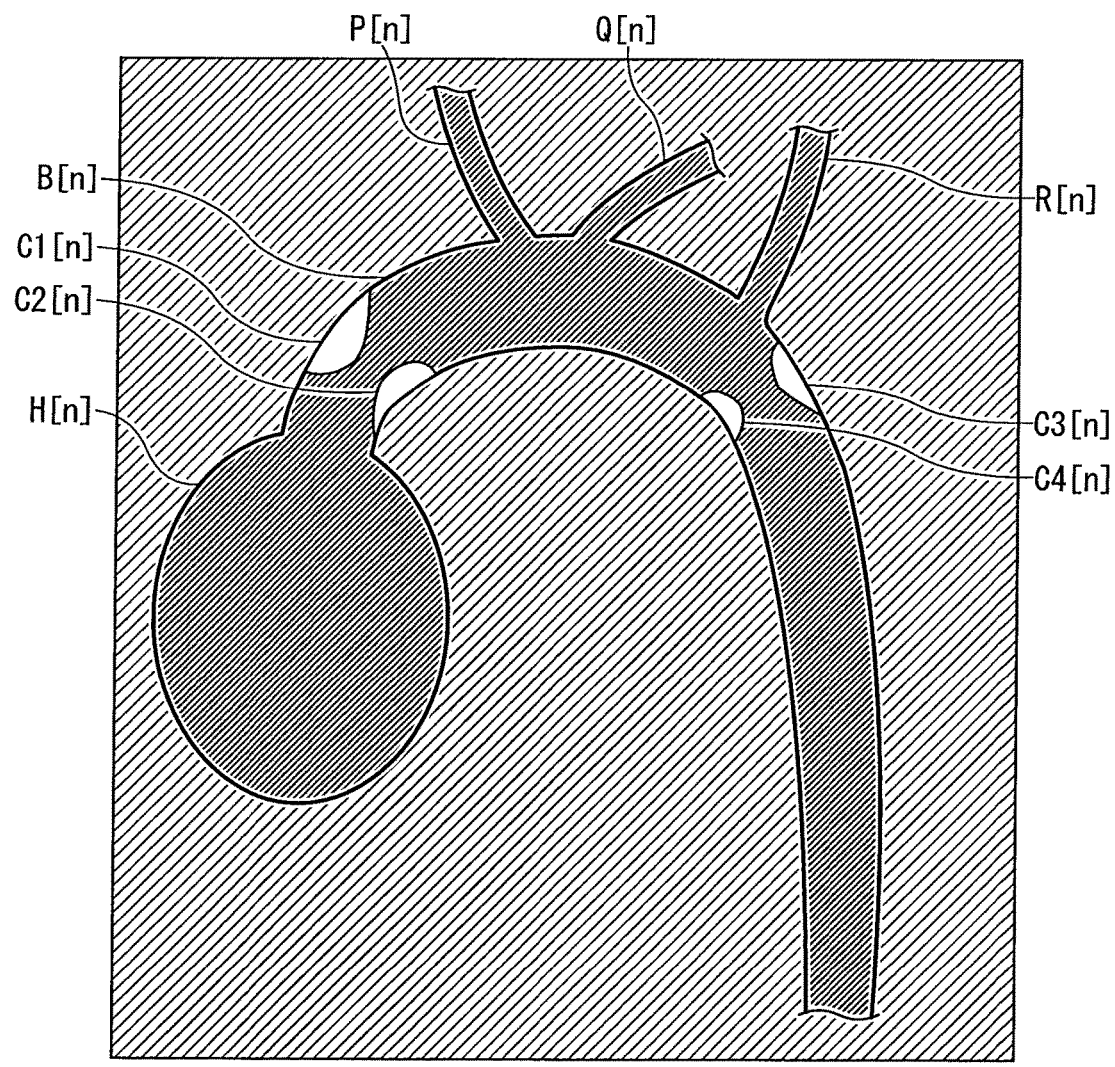
FIG. 6 is a diagram illustrating an example of a fluoroscopic image of an end-systolic heart.

FIG. 5 is a diagram illustrating an example of a fluoroscopic image of the end-diastolic heart. FIG. 6 is a diagram illustrating an example of a fluoroscopic image of the end-systolic heart.

FIG. 5 shows a heart region $H[m]$ of the m-th frame of the first to T-th frames, an aortic arch region $B[m]$ of the aorta above the heart region $H[m]$, a BCA region $P[m]$, an LCA region $Q[m]$ and an LSCA region $R[m]$, the m-th frame corresponding to an end-diastolic period of the heart, and the regions $P[m]$, $Q[m]$ and $R[m]$ being branch arteries branching off from the aortic arch region $B[m]$. Further, calcified regions $C1[m]$ to $C4[m]$ with a high luminance are formed on an inner wall surface of the aortic arch region $B[m]$.

FIG. 6 shows a heart region $H[n]$ of the n-th frame of the first to T-th frames, an aortic arch region $B[n]$ of the aorta above the heart region $H[n]$, a BCA region $P[n]$, an LCA region $Q[n]$ and an LSCA region $R[n]$, the n-th frame corresponding to an end-systolic period of the heart, and the regions $P[n]$, $Q[n]$ and $R[n]$ being branch arteries branching off from the aortic arch region $B[n]$. Further, calcified regions $C1[n]$ to $C4[n]$ with a high luminance are formed on an inner wall surface of the aortic arch region $B[n]$.

Note that the calcified regions $C1[m]$ to $C4[m]$ and $C1[n]$ to $C4[n]$ on the fluoroscopic images illustrated in FIGS. 5 and 6 are hard to recognize visually compared to the image based on the angiographic volume illustrated in FIG. 4.

Returning to the description of FIG. 3, the sub-region image generating unit 72 has a function to generate an image (sub-region image) based on the sub-region volume registered in the sub-region volume storage device 58. Note that the sub-region image generating unit 72 generates the sub-region image as a two-dimensional image or three-dimensional image based on the sub-region volume. The two-dimensional image is a sectional image (including an MPR (multi-planar reconstruction) image) based on the sub-region volume, i.e., an image on a plane parallel to a projection plane of the X-ray fluoroscopy performed by the X-ray fluoroscopic imaging unit 71. The three-dimensional image is based on the sub-region volume, and obtained by fluoroscopic projection in a fluoroscopic direction of the X-ray fluoroscopy performed by the X-ray fluoroscopic imaging unit 71 or by parallel projection on a projection plane of the X-ray fluoroscopy.

The calcified region image generating unit 73 has a function to generate a calcified region image, which is an image obtained by extracting a calcified region from a sub-region image generated by the sub-region image generating unit 72.

Figure 7:
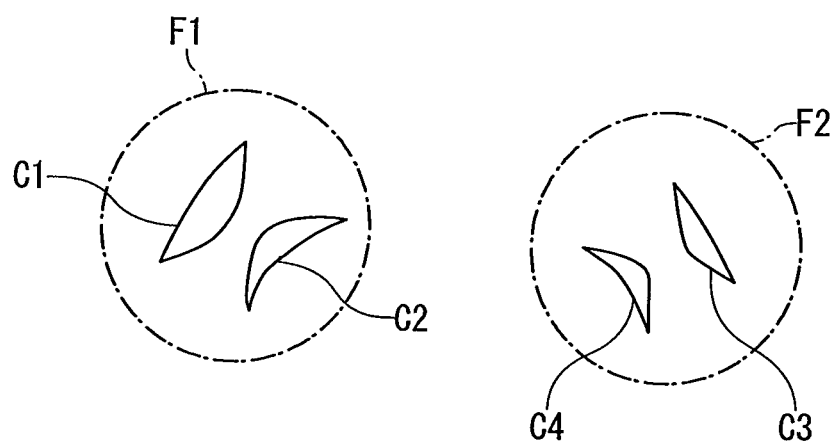
FIG. 7 is a diagram illustrating an example of calcified region images.

FIG. 7 is a diagram illustrating an example of calcified region images.

FIG. 7 shows two calcified region images in the sub-regions (high-curvature regions) F1 and F2 in the angiographic volume illustrated in FIG. 4. The calcified region image in the sub-region F1 contains two high-luminance calcified regions C1 and C2. The calcified region image in the sub-region F2 contains two high-luminance calcified regions C3 and C4.

Returning to the description of FIG. 3, the calcified region detection unit 74 has a function to detect a calcified region on each of the frames of the fluoroscopic images collected by the X-ray fluoroscopic imaging unit 71, using thresholding. The calcified region detection unit 74 may sometimes detect a plurality of calcified regions included in respective sub-regions on each of the fluoroscopic images. In that case, preferably the calcified region detection unit 74 detects calcified regions in plural high-curvature regions based on the curvature factor of blood vessels on each fluoroscopic image as described in relation to the sub-region volume extraction unit 62.

The calcified region detection unit 74 detects calcified regions on each of the fluoroscopic images in response to a command entered by the operator via the input device 56 (illustrated in FIG. 1). In that case, based on the calcified region detected in response to a command entered by the operator via the input device 56 (illustrated in FIG. 1) on the fluoroscopic image of the first frame, the calcified region detection unit 74 automatically detects calcified regions on fluoroscopic images of second and subsequent frames in sequence.

The associating unit 75 has a function to associate (link) the calcified regions on the calcified region image extracted by the calcified region image generating unit 73 with the calcified regions contained in the sub-region (high-curvature region) on the fluoroscopic image of each frame detected by the calcified region detection unit 74. The associating unit 75 associates the calcified regions on the calcified region image with the calcified regions in the sub-region on the fluoroscopic image of each frame based on size, shape, relative positional relationship, and the like. For example, the calcified region C1 (illustrated in FIG. 7) on the calcified region image is associated with a calcified region C1[$m$] (illustrated in FIG. 5) in the sub-region on the fluoroscopic image of the m-th frame or a calcified region C1[$n$] (illustrated in FIG. 6) in the sub-region on the fluoroscopic image of the nth frame.

The aligning unit 76 has a function to align a calcified region image with a sub-region (high-curvature region) on a fluoroscopic image based on positions of the calcified regions in the sub-region on the fluoroscopic image of each frame collected by the X-ray fluoroscopic imaging unit 71 and on positions of the calcified regions on the calcified region image associated with the calcified regions in the sub-region. Regarding each sub-region, the aligning unit 76 aligns the calcified region image with the sub-regions on the fluoroscopic image such that the calcified regions on the calcified region image will overlap the calcified regions in the sub-region on the fluoroscopic image.

The conventional technique aligns the entire calcified region image and the entire fluoroscopic image with each other with reference to bones or other landmarks.

Figure 8:
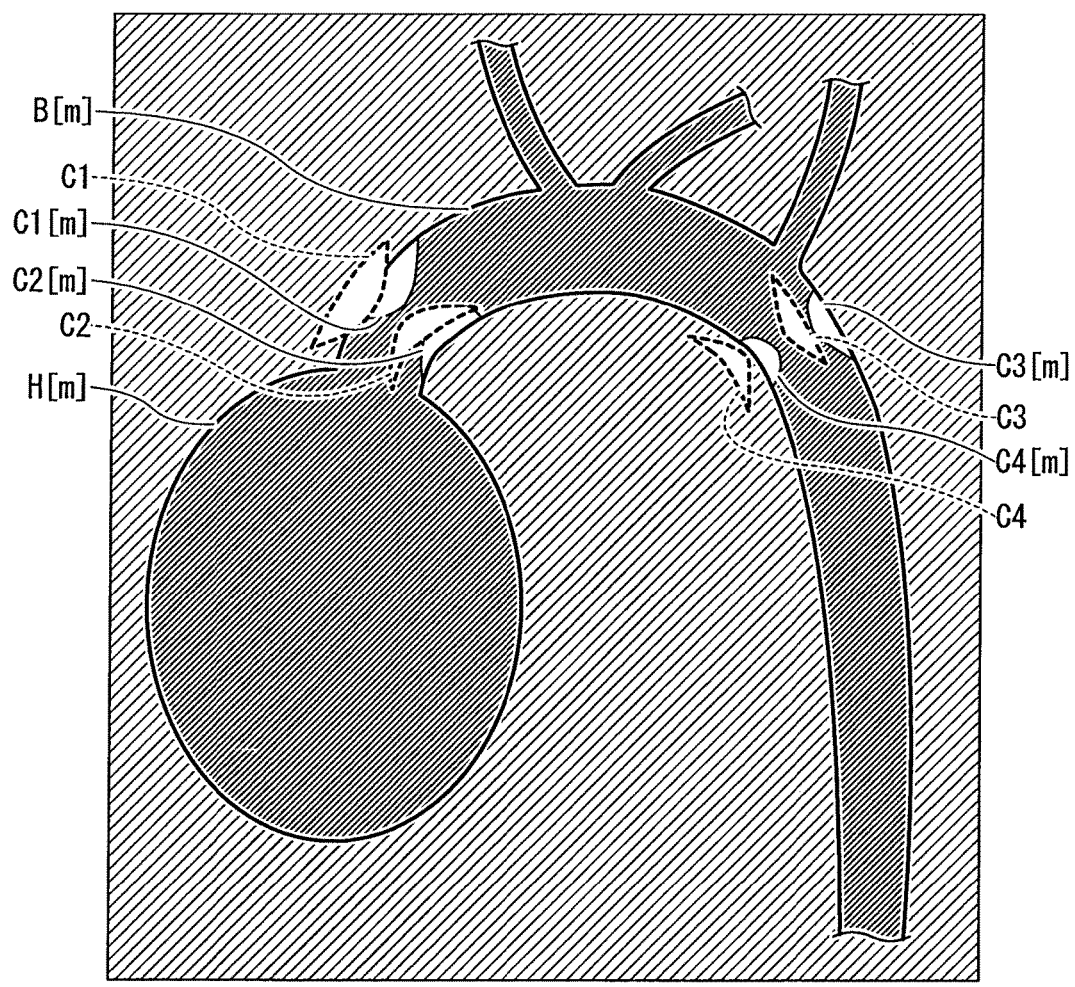
FIG. 8 is a diagram illustrating an angiographic image of a chest aligned with an end-diastolic fluoroscopic image according to a conventional technique.
Figure 9:
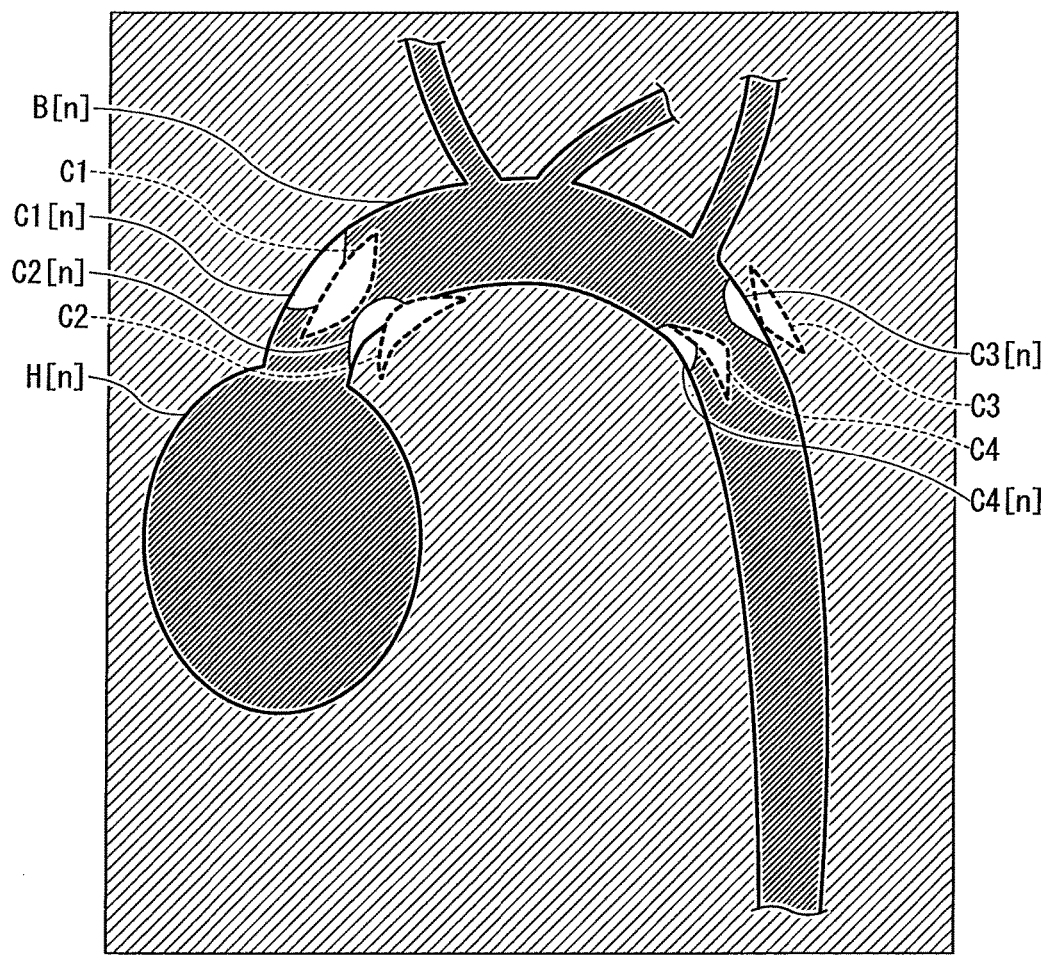
FIG. 9 is a diagram illustrating an angiographic image of a chest aligned with an end-systolic fluoroscopic image according to a conventional technique.

FIG. 8 is a diagram illustrating an angiographic image of the chest aligned with an end-diastolic fluoroscopic image according to the conventional technique. FIG. 9 is a diagram illustrating an angiographic image of the chest aligned with an end-systolic fluoroscopic image according to the conventional technique.

FIG. 8 shows an image which results when the entire angiographic image of the chest is aligned with the fluoroscopic image of the m-th frame illustrated in FIG. 5 using a bone as a landmark. FIG. 9 shows an image which results when an entire angiographic image of the chest is aligned with the fluoroscopic image of the nth frame illustrated in FIG. 6 using a bone as a landmark.

As illustrated in FIG. 8, when a phase of the angiographic image of the chest is not end-diastolic, the calcified regions C1[$m$], C2[$m$], C3[$m$], and C4[$m$] do not coincide in position with the calcified regions C1, C2, C3, and C4, respectively.

As illustrated in FIG. 9, when the phase of the chest angiographic image is not end-systolic, the calcified regions C1[$n$], C2[$n$], C3[$n$], and C4[$n$] do not coincide in position with the calcified regions C1, C2, C3, and C4, respectively.

Figure 10:
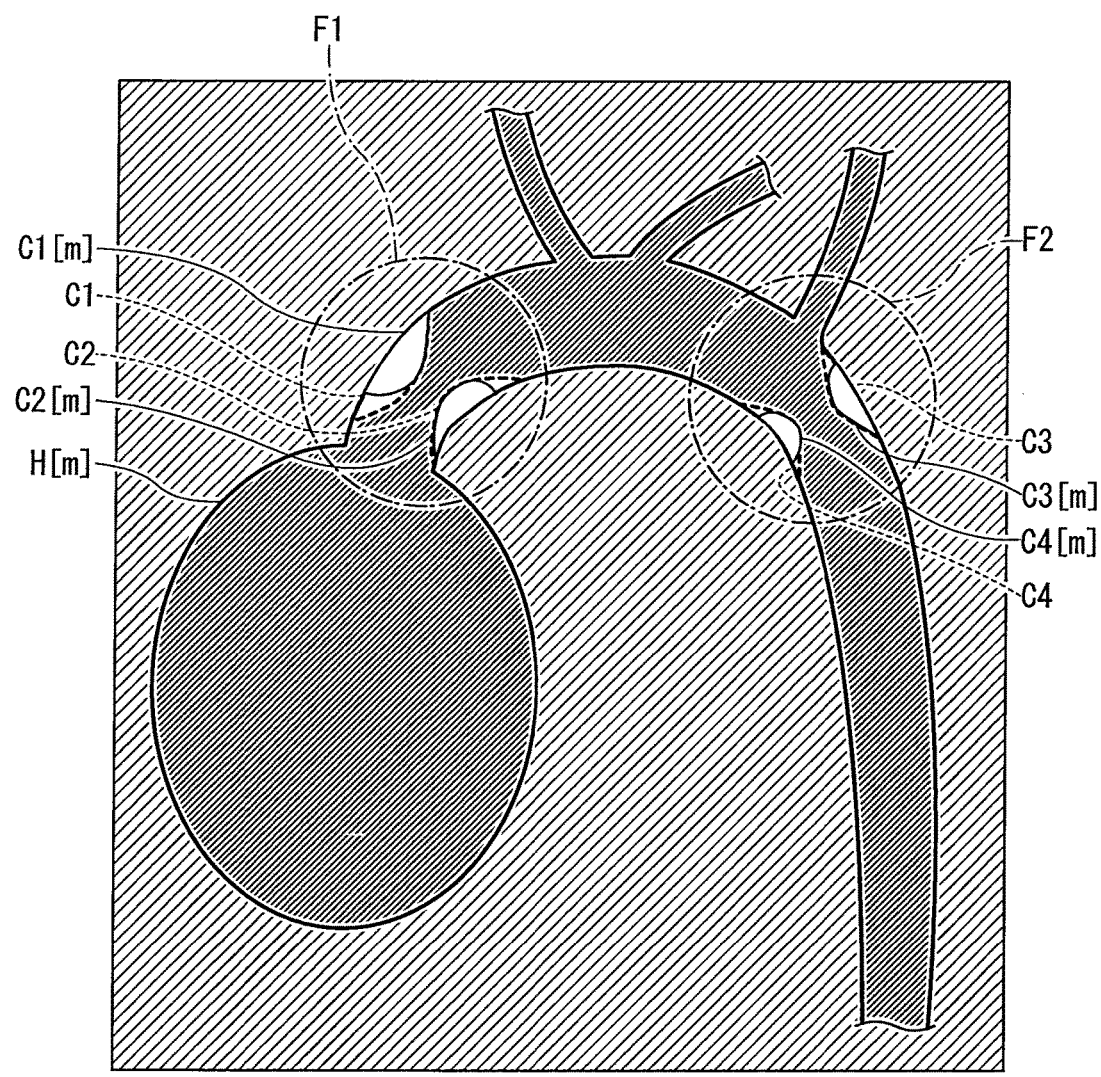
FIG. 10 is a diagram illustrating a calcified region image aligned with sub-regions in an end-diastolic fluoroscopic image by an aligning unit according to the present embodiment.
Figure 11:
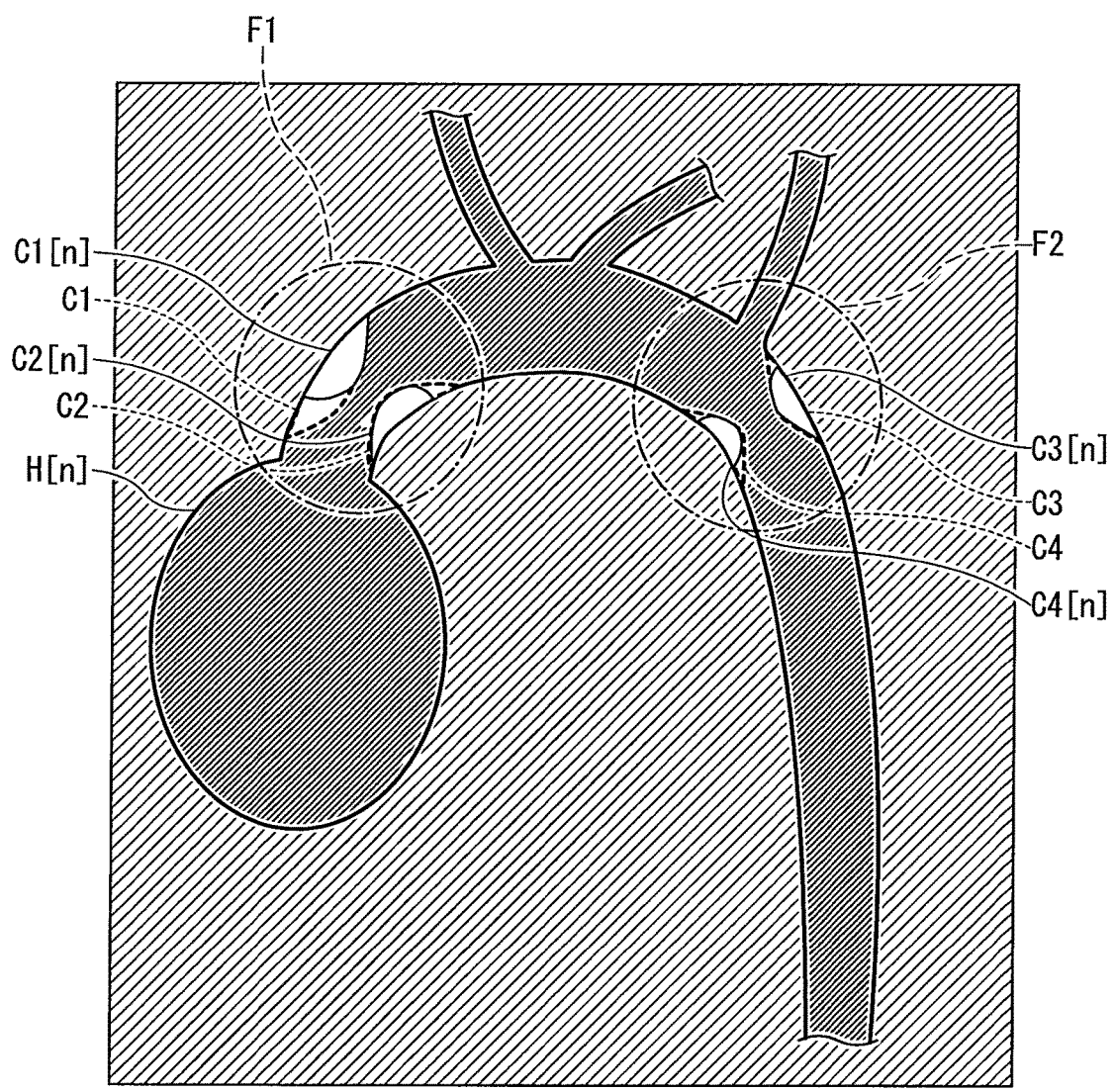
FIG. 11 is a diagram illustrating a calcified region image aligned with sub-regions in an end-systolic fluoroscopic image by the aligning unit according to the present embodiment.

FIG. 10 is a diagram illustrating a calcified region image aligned with sub-regions in an end-diastolic fluoroscopic image by the aligning unit 76 according to the present embodiment. FIG. 11 is a diagram illustrating a calcified region image aligned with sub-regions in an end-systolic fluoroscopic image by the aligning unit 76 according to the present embodiment.

FIG. 10 shows an image which results when a calcified region image is aligned with the sub-region F1 in a fluoroscopic image based on the calcified regions C1[$m$] and C2[$m$] in the sub-region F1 on the end-diastolic fluoroscopic image illustrated in FIG. 5 and the calcified regions C1 and C2 on the calcified region image and when a calcified region image is aligned with the sub-region F2 in a fluoroscopic image based on the calcified regions C3[$m$] and C4[$m$] in the sub-region on the end-diastolic fluoroscopic image and the calcified regions C3 and C4 on the calcified region image.

FIG. 11 shows an image which results when a calcified region image is aligned with the sub-region F1 in a fluoroscopic image based on the calcified regions C1[$n$] and C2[$n$] in the sub-region F1 on the end-systolic fluoroscopic image illustrated in FIG. 6 and the calcified regions C1 and C2 on the calcified region image and when a calcified region image is aligned with the sub-region F2 in a fluoroscopic image based on the calcified regions C3[$n$] and C4[$n$] in the sub-region F2 on the end-systolic fluoroscopic image and the calcified regions C3 and C4 on the calcified region image.

As illustrated in FIG. 10, even when the phase of a calcified region image is not end-diastolic (illustrated in FIG. 7), since the calcified region image is aligned with the sub-region in the fluoroscopic image with reference to corresponding calcified regions, the calcified regions C1[$m$], C2[$m$], C3[$m$], and C4[$m$] substantially coincide in position with the calcified regions C1, C2, C3, and C4, respectively.

As illustrated in FIG. 11, even when the phase of a calcified region image is not end-systolic (illustrated in FIG. 7), since the calcified region image is aligned with the sub-region in the fluoroscopic image with reference to corresponding calcified regions, the calcified regions C1[$n$], C2[n], C3[n], and C4[n] substantially coincide in position with the calcified regions C1, C2, C3, and C4, respectively.

Returning to the description of FIG. 3, the display control unit 77 has a function to display fused images on the display device 55 in sequence. Each of the fused images is obtained by fusing (superimposing) the calcified region image onto the sub-region on the fluoroscopic image of each frame collected by the X-ray fluoroscopic imaging unit 71, the calcified region image being aligned with the calcified region in the sub-region by the aligning unit 76. The fused image is produced by fusing the calcified region image onto the fluoroscopic image, with the images aligned with each other through real-time synchronization. The display control unit 77 combines the fused image with text information and scales of various parameters and outputs resulting data as a video signal to the display device 55.

The conventional technique uses a display format in which a fixed calcified region C1 is placed on a fluoroscopic image (moving image) containing a calcified region C1[t] which moves periodically along with heartbeats. On the other hand, the display control unit 77 according to the present embodiment uses a display format in which on a fluoroscopic image, a calcified region (sub-region) which moves periodically along with heartbeats is superimposed with a calcified region (calcified region image) according to the movements of the calcified region (sub-region).

Figure 12:
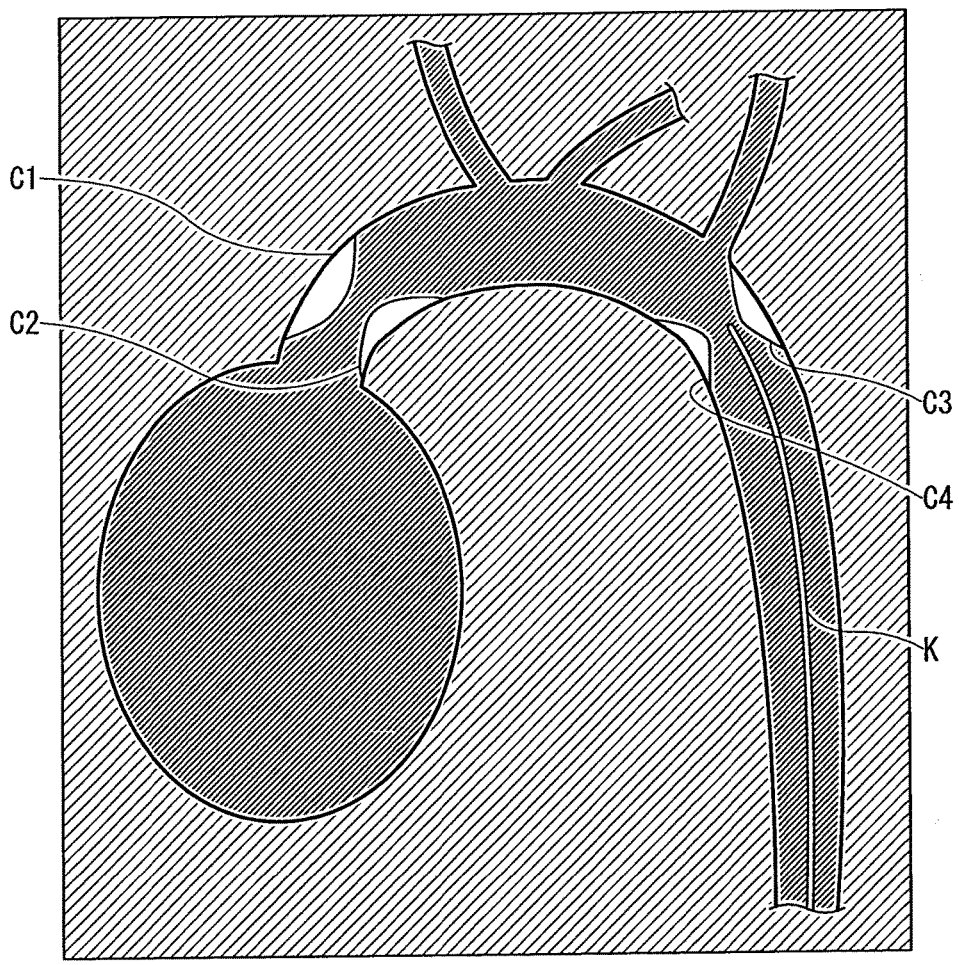
FIG. 12 is a diagram illustrating an example of a fused image which is based on an end-diastolic fluoroscopic image and displayed by a display control unit according to the present embodiment.
Figure 13:
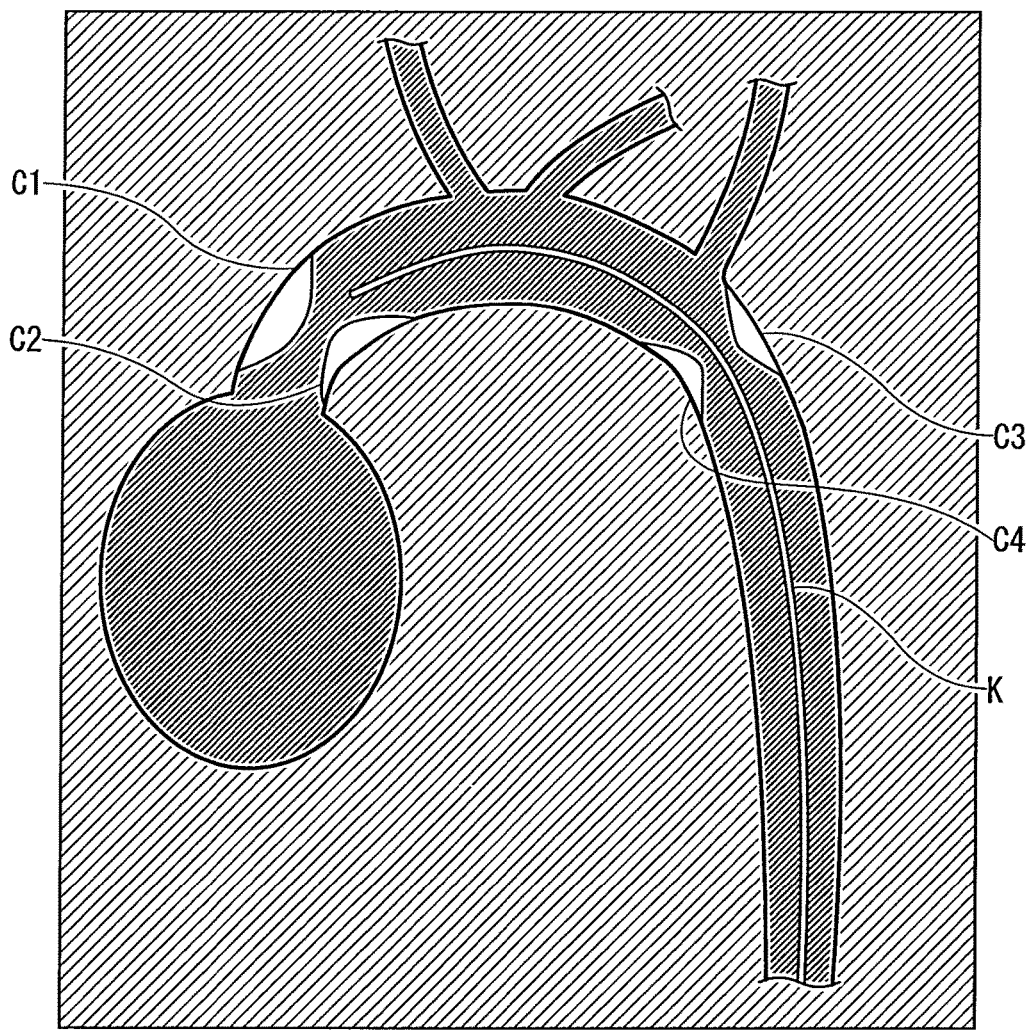
FIG. 13 is a diagram illustrating an example of a fused image which is based on an end-systolic fluoroscopic image and displayed by the display control unit according to the present embodiment.

FIG. 12 is a diagram illustrating an example of a fused image which is based on an end-diastolic fluoroscopic image and displayed by the display control unit 77 according to the present embodiment. FIG. 13 is a diagram illustrating an example of a fused image which is based on an end-systolic fluoroscopic image and displayed by the display control unit 77 according to the present embodiment.

In an aortic valve replacement procedure, as the fused image illustrated in FIG. 12 is displayed, the surgeon can advance a catheter (medical instrument) K while keeping track of positional relationship between the distal end of the catheter K displayed in real time and the calcified regions C3 and C4 aligned through real-time synchronization. When the catheter K is advanced further, as the fused image illustrated in FIG. 13 is displayed, the surgeon can advance the catheter K while keeping track of positional relationship between the distal end of the catheter K displayed in real time and the calcified regions C1 and C2 aligned through real-time synchronization. That is, since the fused images illustrated in FIGS. 12 and 13 are displayed during the aortic valve replacement procedure, it is possible to reduce the risk that the distal end of the catheter K will come into contact with the calcified areas (calcified regions C1, C2, C3, and C4).

The display control unit 77 illustrated in FIG. 3 may have a function to detect the position of the catheter from the fluoroscopic image, and then issue a visual or audible warning to the surgeon when a distance between the position of the catheter advancing through a blood vessel in real time and each calcified region on the calcified region image is equal to or smaller than a threshold. The display control unit 77 may have a function to detect the position of a catheter equipped with a position sensor, and then issue a visual or audible warning to the surgeon when a distance between the position of the catheter advancing through a blood vessel in real time and each calcified region on the calcified region image is equal to or smaller than a threshold.

Next, operation of the X-ray diagnostic apparatus 1 according to the present embodiment will be described with reference to FIGS. 1, 14, and 15.

Figure 14:
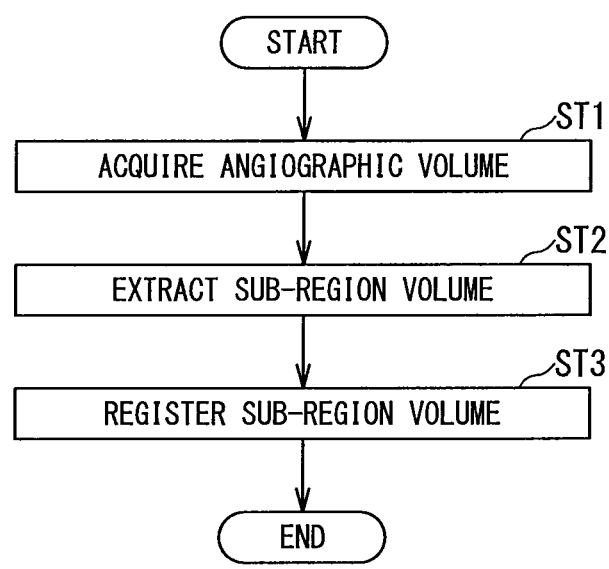
FIG. 14 is a flowchart illustrating one of operation of the X-ray diagnostic apparatus according to the present embodiment.
Figure 15:
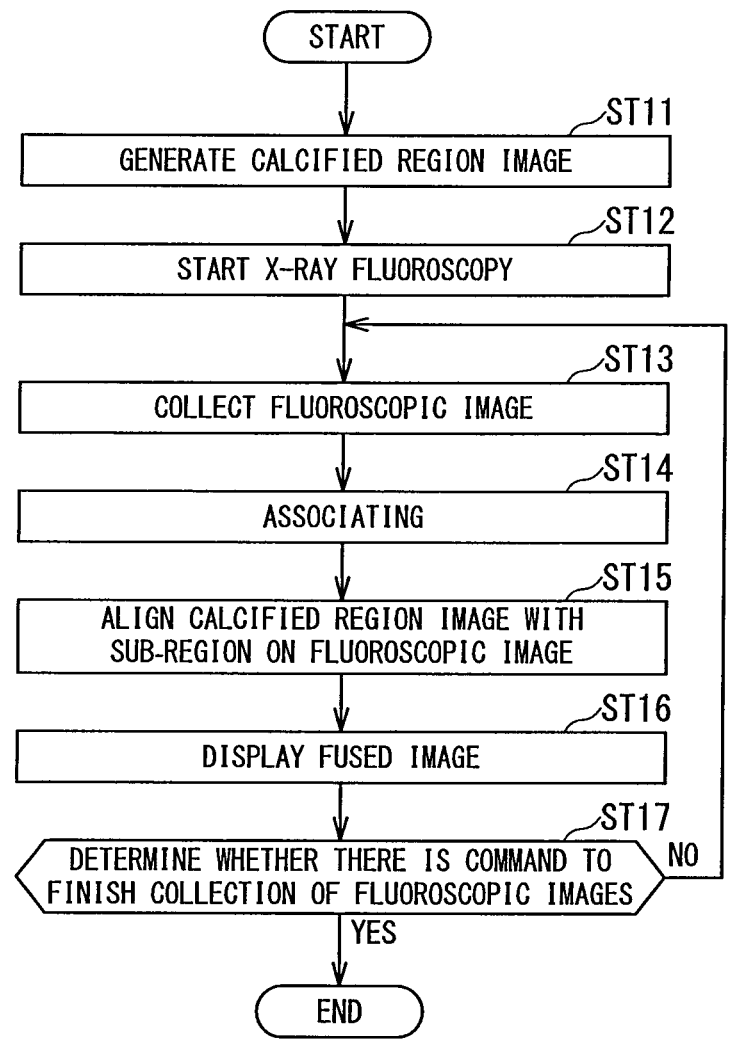
FIG. 15 is a flowchart illustrating one of operation of the X-ray diagnostic apparatus according to the present embodiment.

FIGS. 14 and 15 are flowcharts illustrating operation of the X-ray diagnostic apparatus 1 according to the present embodiment. Note that whereas steps ST1 to ST3 illustrated in FIG. 14 are carried out before surgery-related X-ray fluoroscopy, steps ST11 to ST17 illustrated in FIG. 15 are carried out during the surgery-related X-ray fluoroscopy.

First, the X-ray diagnostic apparatus 1 illustrated in FIG. 1 acquires an angiographic volume (illustrated in FIG. 4) of the chest of the object S including the aorta from the network N via the IF 57 as illustrated in FIG. 14 (step ST1). For example, the X-ray diagnostic apparatus 1 acquires the angiographic volume generated by MR angiography or CT angiography.

The X-ray diagnostic apparatus 1 extracts a sub-region volume (illustrated in FIG. 7) based on the angiographic volume acquired in step ST1 (step ST2). The X-ray diagnostic apparatus 1 registers the sub-region volume extracted in step ST2 in the sub-region volume storage device 58 (step ST3).

Moving to the description of FIG. 15, after the object S is put on the table 31 of the imaging device 2, in response to a command entered via the input device 56, alignment is done by driving the imaging device 2 and bed system 3 via the controller 4 (both illustrated in FIG. 1). Then, the X-ray diagnostic apparatus 1 acquires the sub-region volume registered in step ST3 (illustrated in FIG. 14) and generates a calcified region image concerning a calcified region in a sub-region on the sub-region volume (step ST11).

Upon receiving a command to start collecting fluoroscopic images, the X-ray diagnostic apparatus 1 performs surgery-related X-ray fluoroscopy with respect to the chest of the object S including the aorta by operating the X-ray emitting device 21, X-ray detection device 22, and high voltage generating device 23 (step ST12) and collects a fluoroscopic image (illustrated in FIGS. 5 and 6) of the t-th frame (step ST13). Then, a procedure, such as an aortic valve replacement procedure, in which the surgeon inserts a catheter into the object S is started.

The X-ray diagnostic apparatus 1 associates the calcified region on the calcified region image generated in step ST11 with the calcified region in the sub-region on the fluoroscopic image of the t-th frame collected in step ST13 (step ST14). Then, based on the position of the calcified region in the sub-region on the fluoroscopic image of the t-th frame collected in step ST13 and the position of the calcified region on the calcified region image associated in step ST14, the X-ray diagnostic apparatus 1 aligns the calcified region image with the sub-region on the fluoroscopic image of the t-th frame (step ST15).

The X-ray diagnostic apparatus 1 obtains a fused image (illustrated in FIGS. 12 and 13) by fusing (superimposing) the calcified region image aligned in step ST15 onto the sub-region on the fluoroscopic image of the t-th frame collected in step ST13 and displays the fused image on the display device 55 (step ST16).

The X-ray diagnostic apparatus 1 determines whether or not there is a command to finish the collection of fluoroscopic images started in step ST13 (step ST17). If the result of determination in step ST17 is YES, i.e., if it is determined that there is a command to finish the collection of fluoroscopic images, the X-ray diagnostic apparatus 1 finishes the operation.

On the other hand, if the result of determination in step ST17 is NO, i.e., if it is determined in step ST17 that there is no command to finish the collection of fluoroscopic images, the X-ray diagnostic apparatus 1 collects a fluoroscopic image of the next (t+1)-th frame (step ST13).

With the X-ray diagnostic apparatus 1 according to the present embodiment, since calcified region images containing calcified regions located at positions corresponding to each frame is fused onto sub-regions on the fluoroscopic image of each frame, even if position changes occur on the fluoroscopic image due to heartbeats, an image can be displayed with appropriate calcified region images fused thereon according to the position changes. Thus, the X-ray diagnostic apparatus 1 according to the present embodiment supports a catheter advancing procedure which can avoid contact with calcified areas.

(Variation)

Since the data registered in the sub-region volume storage device 58 illustrated in FIG. 3 is three-dimensional data, the calcified region image generating unit 73 can calculate three-dimensional information about each calcified region on a calcified region image. The calcified region image generating unit 73 calculates property information which represents at least one of volume and thickness (maximum height from a blood vessel wall) of each calcified region on the calcified region image. In that case, the display control unit 77 displays the fused image on the display device 55 by further fusing the property information thereon. In so doing, the display control unit 77 can use at least any of arrows, character display, and numeric values for the fused property information.

The display control unit 77 may be configured to switch information about the calcified regions C1-C4 fused on the fluoroscopic image to property information when there is a switching action via the input device 56.

Figure 16:
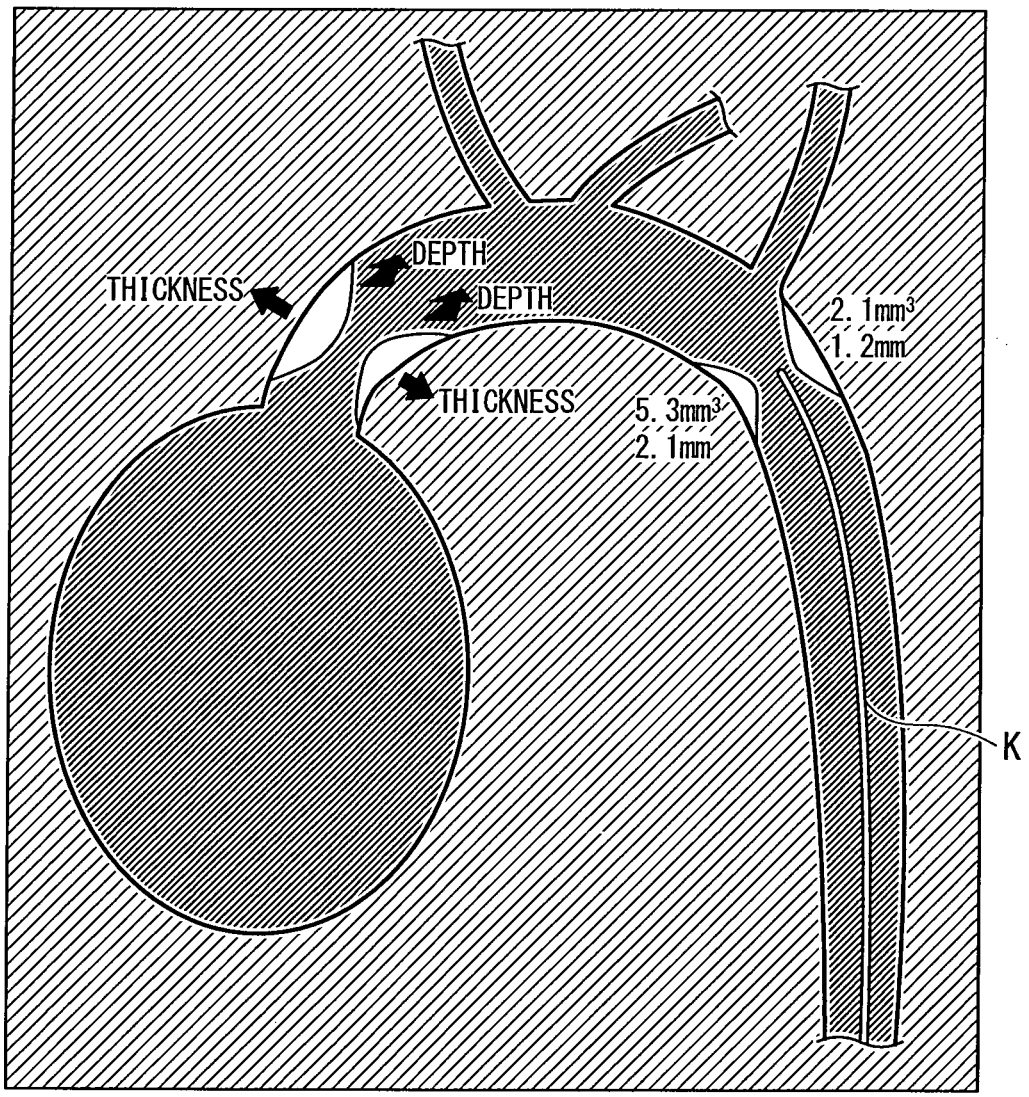
FIG. 16 is a diagram illustrating an example of a fused image with property information fused thereon.

FIG. 16 is a diagram illustrating an example of a fused image with property information fused thereon.

FIG. 16 shows a fused image produced by further fusing property information onto the fused image illustrated in FIG. 12. On the fused image illustrated in FIG. 16, property information which indicates volume and thickness is fused onto a portion which shows each calcified region. The volume as property information is indicated by numeric values such as 2.1 mm$^3$ and 5.3 mm$^3$. The thickness as property information is indicated by numeric values such as 1.2 mm and 2.1 mm.

The thickness as property information is indicated by length of the arrow. Furthermore, since each calcified region has three-dimensional information, depth direction as well as length in the depth direction may be indicated as property information. In FIG. 16, the depth direction and the length in the depth direction as property information are indicated by arrow direction and length.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
   an X-ray emitting device configured to generate X-rays;
   an X-ray detection device placed facing the X-ray emitting device and configured to detect the X-rays; and
   processing circuitry configured to:
      generate a plurality of frames of fluoroscopic images of an object on a basis of the detected X-rays in sequence,
      detect a first calcified region on each of the fluoroscopic images in sequence,
      superimpose a calcified region image on a position of the first calcified region on each of the fluoroscopic images in sequence, the calcified region image including a second calcified region on a pre-acquired CT image or MR image of the object,
      display resulting images on a display device in sequence, and
      notify a user on a basis of a position of a medical instrument inserted into the object and the position of the first or second calcified region.

2. The X-ray diagnostic apparatus according to claim 1, wherein the processing circuitry is further configured to detect a plurality of calcified regions included in respective sub-regions on each of the fluoroscopic images.

3. The X-ray diagnostic apparatus according to claim 2, wherein the processing circuitry is further configured to detect the calcified regions included in the respective sub-regions on a basis of a curvature factor of a blood vessel on each of the fluoroscopic images.

4. The X-ray diagnostic apparatus according to claim 1, wherein the processing circuitry is further configured to detect the calcified region on each of the fluoroscopic images in response to a command entered by a user via an input device.

5. The X-ray diagnostic apparatus according to claim 4, wherein the processing circuitry is further configured to automatically detect, on a basis of the first calcified region detected on a first frame of the fluoroscopic images in response to the command, the first calcified regions on second and subsequent frames of the fluoroscopic images in sequence.

6. The X-ray diagnostic apparatus according to claim 1, wherein the processing circuitry is further configured to notify the user when a distance between the medical instrument and the first or second calcified region falls below a predetermined value.

7. The X-ray diagnostic apparatus according to claim 6, wherein the position of the medical instrument is detected on each of the fluoroscopic images.

8. The X-ray diagnostic apparatus according to claim 6, wherein the position of the medical instrument is detected by a position sensor attached to the medical instrument.

9. The X-ray diagnostic apparatus according to claim 6, wherein the processing circuitry is further configured to notify the user through a sound or a display on the display device.

10. The X-ray diagnostic apparatus according to claim 1, wherein the processing circuitry is further configured to:
    superimpose information about a volume or thickness of calcification on the calcified region image on each of the fluoroscopic images in sequence, and
    display resulting images on the display device in sequence.

11. The X-ray diagnostic apparatus according to claim 1, wherein the processing circuitry is further configured to:
    align the calcified region image with sub-regions including the first calcified region on each of the fluoroscopic images in sequence,
    superimpose the aligned calcified region image with each of positions of the first calcified regions in sequence, the first calcified regions being on the respective fluoroscopic images, and
    display resulting images on the display device in sequence.

12. The X-ray diagnostic apparatus according to claim 1, wherein
the processing circuitry is further configured to extract the second calcified region included in a pre-acquired CT image or MR image of the object as a part thereof in sequence, the second calcified region on the pre-acquired CT image or MR image corresponding to the first calcified region on each of the fluoroscopic images.

13. A display method comprising:
generating a plurality of frames of fluoroscopic images of an object on a basis of detected X-rays in sequence;
detecting a first calcified region on each of the fluoroscopic images in sequence;
superimposing a calcified region image on a position of the first calcified region on each of the fluoroscopic images in sequence, the calcified region image including a second calcified region on a pre-acquired CT image or MR image of the object;
displaying resulting images on a display device in sequence; and
notifying a user on a basis of a position of a medical instrument inserted into the object and the position of the first or second calcified region.

14. The display method according to claim 13, further comprising:
detecting a plurality of the first calcified regions included in respective sub-regions on each of the fluoroscopic images.

15. The display method according to claim 13, further comprising:
detecting the first calcified region on each of the fluoroscopic images in response to a command entered by a user via an input device.

16. The display method according to claim 13, further comprising:
notifying the user when a distance between the medical instrument and the first calcified region falls below a predetermined value.

17. The display method according to claim 16, wherein the position of the medical instrument is detected on each of the fluoroscopic images.

18. The display method according to claim 16, wherein the position of the medical instrument is detected by a position sensor attached to the medical instrument.

19. The display method according to claim 16, further comprising:
notifying the user through a sound or a display on the display device.

* * * * *